United States Patent [19]

Conti

[11] Patent Number: 4,989,446
[45] Date of Patent: Feb. 5, 1991

[54] ULTRASOUND CALIBRATOR

[75] Inventor: James C. Conti, Galena, Mo.

[73] Assignee: Dynatek Laboratories, Inc., Galena, Mo.

[21] Appl. No.: 468,568

[22] Filed: Jan. 23, 1990

[51] Int. Cl.[5] .......................................... G01F 25/00
[52] U.S. Cl. ............................................................. 73/3
[58] Field of Search ................................. 73/1 DV, 3

[56] References Cited

U.S. PATENT DOCUMENTS

| | | |
|---|---|---|
| 3,780,577 | 12/1973 | Brown . |
| 3,981,191 | 9/1976 | Brown et al. . |
| 4,144,752 | 3/1979 | Lalk . |
| 4,372,166 | 2/1983 | Leaeland . |
| 4,381,663 | 5/1983 | Swanson . |
| 4,509,373 | 4/1985 | Brown . |
| 4,546,642 | 10/1985 | Swanson . |
| 4,674,317 | 6/1987 | Cohrs et al. . |
| 4,690,002 | 9/1987 | Hubbard et al. ............... 73/861.25 |
| 4,729,247 | 3/1988 | Brown ................................. 73/3 |
| 4,759,374 | 7/1988 | Kierney et al. ............... 73/861.25 |
| 4,762,012 | 8/1988 | Brown . |

FOREIGN PATENT DOCUMENTS 163378  12/1964  U.S.S.R. ................................. 73/3

Primary Examiner—Robert Raevis
Attorney, Agent, or Firm—Litman McMahon & Brown

[57] ABSTRACT

An ultrasound calibrator apparatus and method for calibrating ultrasound equipment. The apparatus includes a pair of opposed bellows oscillatorily transferring a fluent medium back and forth through a channel with a well-defined cross-sectional area such that the flow velocity therethrough is known. A probe in communication with ultrasound equipment to be tested is submerged in a reservoir which is situated in close proximity to the channel such that the flow velocity can be measured therewith. The ultrasound equipment is then adjusted to correct the discrepancies between the known and measured velocities so as to calibrate the ultrasound equipment.

13 Claims, 2 Drawing Sheets

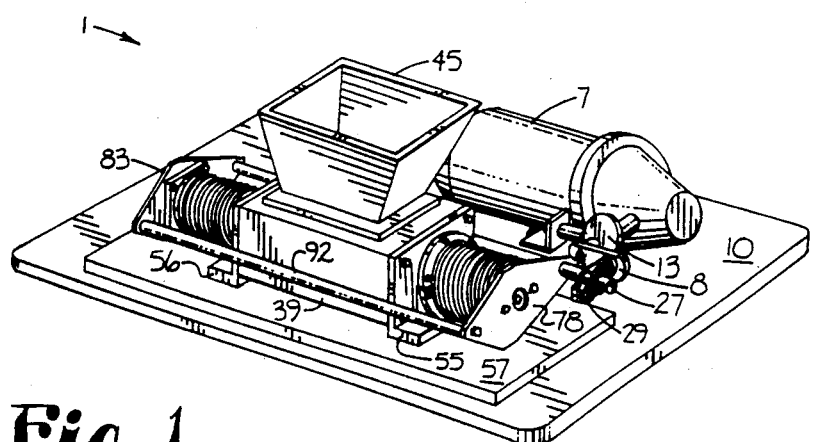
Fig. 1.
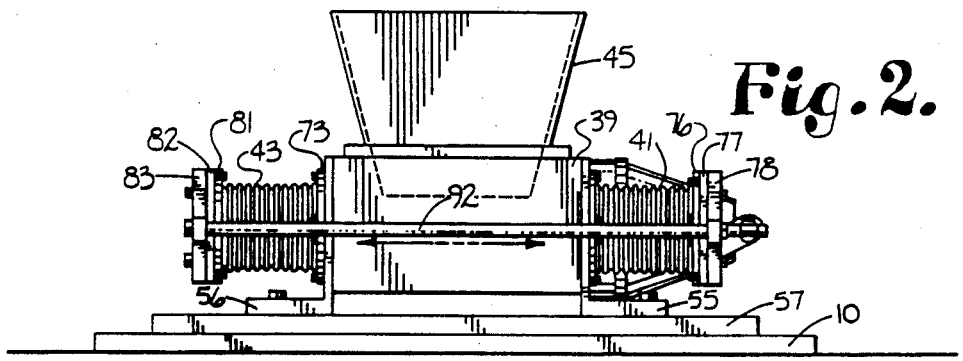
Fig. 2.
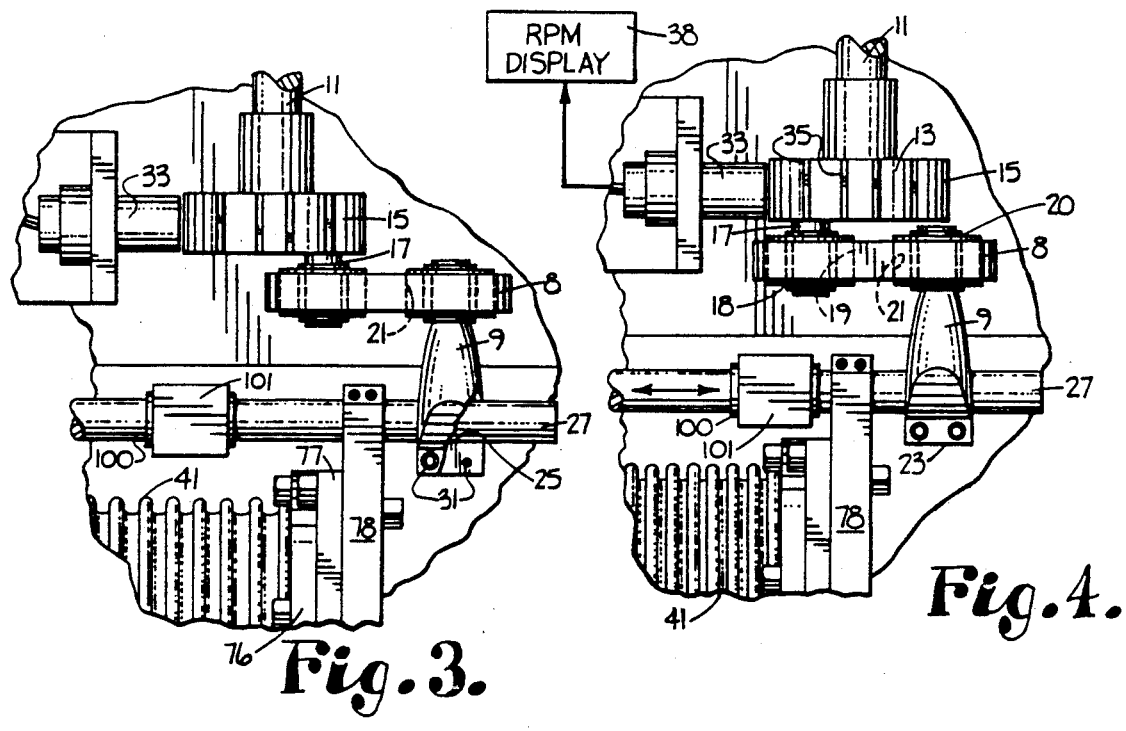
Fig. 3.
Fig. 4.

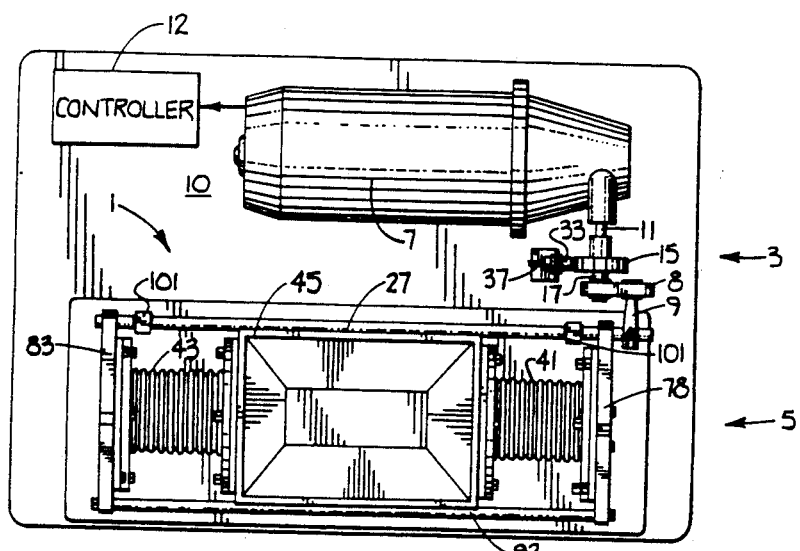
Fig.5.
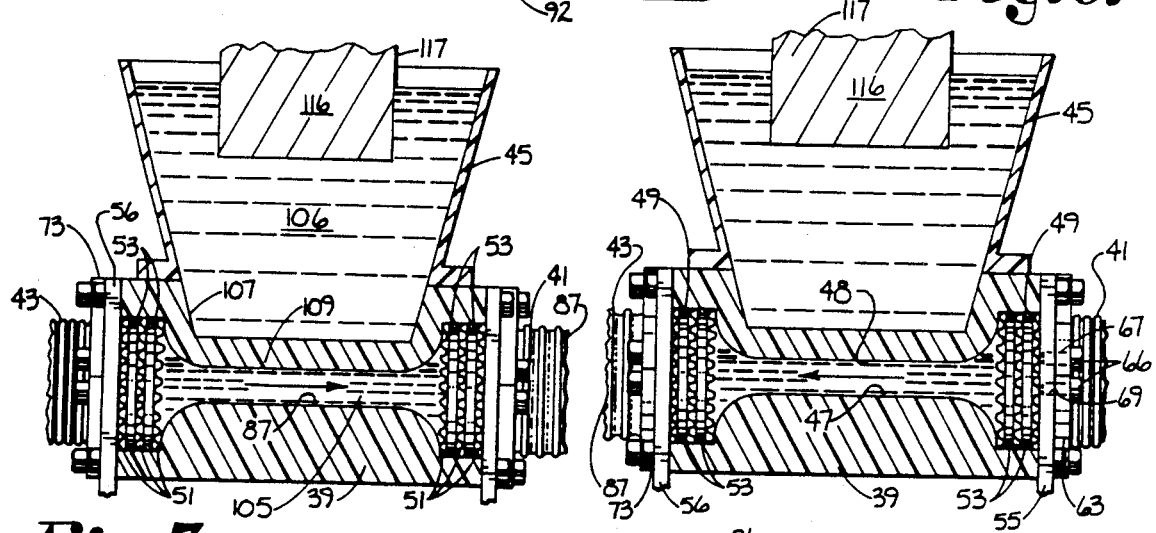
Fig.6.
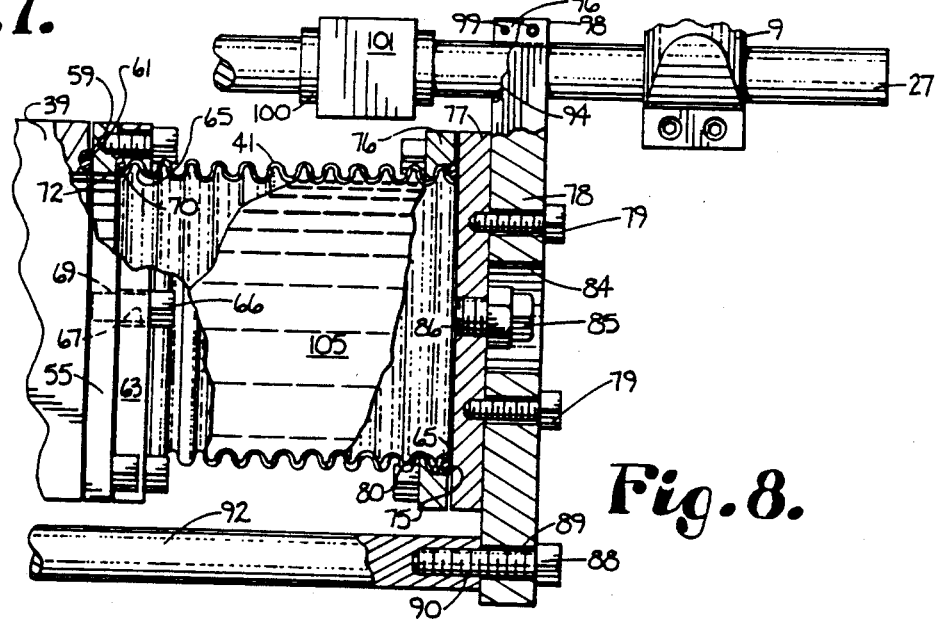
Fig.7.
Fig.8.

ULTRASOUND CALIBRATOR

BACKGROUND OF THE INVENTION

The present invention relates generally to an apparatus and method to be utilized for the calibration of ultrasound equipment and, more particularly, to an apparatus and a method for calibrating the ultrasound equipment used to determine the velocity of flowing fluids.

Ultrasound devices are commonly used in a variety of applications. Typically, such devices can be operated in two different modes: a b-mode or a doppler mode. When operated in the b-mode, an ultrasound device can be used to evaluate certain structural dimensions and characteristics. When operated in the doppler mode, an ultrasound device can be used to evaluate the velocity of flow of a fluent medium.

A major concern in the utilization of ultrasound devices is proper calibration of the device such that measured data can be accurately interpreted. Various approaches have been attempted to provide such calibration, including comparing the signals received from an oscillator transmitting upstream in a flowing media with those received from transmitting downstream.

When making such direct comparisons, extraordinarily stringent precision is required of the various components with a corresponding capital expenditure for the necessary equipment, including certain circuit configurations, high quality operational amplifiers and precision components. Further, the accuracy and stability of the oscillators or multivibrators are very difficult to maintain.

Because of the inherent inaccuracies and expense of equipment needed to reliably calibrate ultrasound equipment, many of the significant applications of such equipment, particularly when operated in the doppler mode, have been largely neglected due to non-availability of convenient relatively inexpensive calibration techniques.

SUMMARY OF THE INVENTION

In the application of the apparatus and method of the present invention, ultrasound flow measurement instruments useful for medical applications and other purposes, such as detecting the flow rate of body fluids through various blood vessels and organs can be calibrated. Such flow measurement instruments measure flow rates within the human body by generating an ultrasound signal in the area where the flow measurement is to be made and the flowing fluid reflects the ultrasound signal back to a sensing device. Naturally, such ultrasound flow meters must be calibrated for specific applications since relatively minor variations in the geometry of the flow channel, the density of the fluid, and the dynamic response behavior of the fluid flowing through a channel under various environments will vary the response behavior to ultrasound signals.

The present invention is an ultrasound equipment calibration apparatus for use in conjunction with ultrasound equipment wherein the apparatus comprises a bellows, a flow channel, and a transmission reservoir. Fluid contained in a first set of bellows is forced by a driving mechanism through the flow channel and into a second set of bellows. A gearhead motor drives a bellows which, when compressed, forces the fluid contained therein through the flow path and into the synchronized receiving bellows. Because the fluid capacity and rate of compression of the bellows is precisely known or can be precisely calculated, a velocity profile of the fluent medium through the channel is readily obtainable at the same time that the ultrasound equipment measures the velocity of the fluent medium in the channel, such that the results measured by the ultrasound equipment can be compared with the relatively very precise velocity profiles developed by use of the apparatus. The ultrasound equipment is then adjusted such that the flow measurement output thereof matches the velocity profile of the calibration apparatus.

Prior to the application of the present invention, no true flow velocity calibration for ultrasound equipment was readily available.

PRINCIPAL OBJECTS OF THE INVENTION

Therefore, the principal objects of the present invention are: to provide an apparatus and a method for calibrating ultrasound equipment; to provide such an apparatus and a method which is mechanically simple in design and function; to provide such an apparatus and a method which is reliable in operation; to provide such an apparatus and a method wherein test fluid is easily filled and emptied; to provide such an apparatus which is easily cleaned; and to provide such an apparatus which is economical to manufacture, efficient in operation, capable of a long operating life and particularly well adapted for the proposed use thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of an ultrasound calibrator apparatus in accordance with the present invention.

FIG. 2 is an enlarged side elevational view of the apparatus.

FIG. 3 is an enlarged, fragmentary, top plan view of the apparatus showing a bellows thereof extended with portions broken away to reveal details thereof.

FIG. 4 is a top plan view of the apparatus similar to that of FIG. 3, but with the bellows compressed.

FIG. 5 is an enlarged top plan view of the apparatus.

FIG. 6 is an enlarged, fragmentary, cross-sectional view of the apparatus showing fluid in a calibration chamber flowing leftwardly.

FIG. 7 is a cross-sectional view of the apparatus similar to that of FIG. 6, but with the fluid flowing rightwardly.

FIG. 8 an enlarged, fragmentary, top plan view of the apparatus, showing the bellows with portions broken away to reveal details thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally designates an ultrasound calibrator apparatus embodying the present invention. The apparatus 1 comprises driving means such as the illustrated eccentricity driver assembly 3 and conduit means such as the illustrated fluid flow assembly 5.

The driver assembly 3 includes motor means or a prime mover such as the illustrated electric motor 7 and mechanical linkage means, comprising a crank arm 8 and a reciprocating shaft 9. Typically, the motor 7 is a variable speed motor capable of operating at rotational speeds of 60-120 revolutions per minute, (a suitable motor is Model No. 4Z728 as manufactured by Dayton of Chicago, IL). The speed of the motor 7 can be controlled with a speed controller 12, as schematically indicated in FIG. 5, such as the controller available as Model No. 946 as manufactured by Bodine of Long Island City, New York.

The motor 7 is rigidly secured to a platform 10. A rotary drive shaft 11 operatively driven by the motor 7 is rigidly secured to an eccentric cam 13 having a circumferential periphery 15 and which rotates coaxially with the shaft 11. A cam shaft 17 rigidly extends outwardly from the cam 13 in spaced relation to the axis of rotation of the shaft 11 and is rotatably mounted by a journal 18 in a first throughbore 19 of the crank arm 8 such that the cam shaft 17 is pivotally secured therein. The reciprocating shaft 9 is rotatably mounted in a second journal 20 in a second throughbore 21 such that the reciprocating shaft 9 is pivotally secured therein.

Near a distal end 23 of the reciprocating shaft 9 is a transverse throughbore 25 with a diameter which is dimensioned slightly larger than the diameter of a drive rod 27 inserted therethrough. A slot 29 is positioned between the distal end 23 of the reciprocating shaft 9 and the throughbore 25 such that a pair of bolts 31 threadedly extending through the shaft 9 on opposite sides of the slot 29 rigidly clamp the reciprocating shaft 9 to the drive rod 27.

A tachometer sensor 33 is spaced in close proximity to the cam peripheral surface 15 and is rigidly secured to the platform 10. Equidistantly spaced about the cam peripheral surface 15 are a plurality of platelets 35 formed by grooving of the surface 15. The platelets 35 are individually sensed by the tachometer sensor 33 when the shaft 11 and the cam 13 are rotated. Signals generated by the tachometer sensor 33 as a result of rotation of the cam 13 are communicated by an electrical cable 37 to an auxiliary supporting RPM display device 38, as schematically indicated in FIG. 4. A suitable tachometer sensor 33 and a display device 38 are available as Model No. ACT-1A and Model No. M-190 as manufactured by Monarch of Amherst, New Hampshire. For example, in the illustrated embodiment, there are ten such platelets equidistantly spaced at 36° intervals such that each ten signals generated by the sensor 33 signifies one revolution of the cam 13. Accordingly, the total number of signals per minute divided by ten yields the rotational velocity of the cam in revolutions per minute.

The fluid flow assembly 5 comprises a flow block 39, first and second compressible bellows means for holding a fluent medium and dispersing or receiving a generally fixed quantity of the fluent medium for a given movement thereof (for example, a fixed amount of fluid for fixed amounts of translational movement), such as illustrated first bellows 41 and second bellows 43, and interfacing means such as illustrated reservoir 45. Suitable bellows for use as the bellows 41 and 43 are available as Model No. SK-12582 as manufactured by Servometer of Cedar Grove, NJ. The block 39 is preferably constructed of acrylic plastic, polyvinylidenedifluoride, or other suitable material which has a relatively low acoustic impedance. A flow channel 47 passes axially through the center of the block 39 and is aligned from right to left as shown in FIGS. 6 and 7. The flow channel 47 preferably has a cross-section which is substantially circular in nature. The channel 47 of the illustrated embodiment has a central cylindrical portion 48 having an internal diameter of approximately 20 mm.

Where the flow channel 47 approaches opposite ends of the block 39, the flow channel 47 smoothly tapers outwardly to a diameter which is dimensioned approximately the same size as that of the diameter of the bellows 41 and 43 as shown in FIGS. 6 and 7, with each end of the flow channel 47 having a screen cavity 49 situated immediately adjacent to each end of the block 39. Positioned within each of the screen cavities 49 is a plurality of screens 51. Annular spacers 53 are imposed between the screens 51 to maintain uniform horizontal spacing therebetween. The spacers 53 are constructed of acrylic plastic or other suitable material. In the illustrated embodiment, each screen cavity 49 contains three 100-mesh screens with the screens spaced $\frac{1}{4}$-inch apart by annular acrylic rings having a radial thickness of $\frac{1}{8}$ inch.

A pair of L-shaped brackets 55 and 56 are rigidly secured to each end of the block 39. Each bracket 55 and 56 has a circular groove 59 facing the block 39 with an O-ring 61 contained therein so as to provide a fluid tight seal between the brackets 55 and 56 and the block 39. The brackets 55 and 56 are preferably constructed of stainless steel or other suitable material and are rigidly secured to a plate 57 which, in turn, is rigidly secured to the platform 10, as shown in FIG. 2.

A bellows clamp 63, which is preferably constructed of anodized aluminum or other suitable material, is split into two semi-circular portions such that a lip 65 of the clamp 63 can be inserted into a convolution of the bellows 41 near one end thereof. A plurality of bolts 66 passing through bores 67 mate with tapped bores 69 in the bracket 55. An O-ring 70 sandwiched between the end of the bellows 41 and the bracket 55 and compressed by the clamping action of the bellows clamp 63 when the bolts 66 are threadedly advanced in tapped bores 69 in the bracket 55 forms a liquid-tight seal between the bellows 41 and the bracket 55.

A bore 72 through the bracket 55 is axially aligned with the screen cavity 49 such that the interior of the bellows 41 flow communicates with the screen cavity 49 and the flow channel 47.

In the same manner as described for the bellows 41, the bellows 43 is rigidly secured by a mirror image mechanism including a bellows clamp 73 to the bracket 56 forming liquid-tight seal between the bellows 43 and the block 39.

A distal end of the bellows 41 is rigidly secured by a bellows clamp 76 to a closure plate 77 and sealed with an O-ring 75 positioned in a groove 80 between the bellows clamp 76 and the closure plate 77, similarly to that hereinbefore described, for forming liquid-tight seals about the opposite end of the bellows 41. The closure plate 77, in turn, is rigidly secured to a reciprocating drive plate 78, such as with bolts 79 as illustrated in FIG. 8.

Similarly, a distal end of the bellows 43 is rigidly secured by a bellows clamp 81 to a closure plate 82 which is rigidly secured to a drive plate 83 by a mechanism that is substantially a mirror image of the mechanism sealing the distal end of the bellows 41. The plates 78 and 83 are preferably constructed of aluminum or other suitable material.

A bore 84 in each of the drive plates 78 and 83 provides clearance for plugs 85 which are threadedly or otherwise secured in tapped throughbores or ports 86 in the closure plates 77 and 82. The plugs 85 are appropriately spaced to serve as fill ports whereby one of such fill ports is used to introduce fluid into a composite cavity 87 comprising the interior channel 47 and cavities of the block 39, the bellows 41 and 43, and the brackets 55 and 56, while the other such fill port is used to bleed air from the composite cavity 87.

Bolts 88 are positioned through bores 89 in drive plates 78 and 83 and threadedly advanced into tapped bores 90 in a rail 92 opposite the drive rod 27 so as to rigidly secure the drive plates 78 and 83 relative to each other. Directly opposite the bores 89 in the drive plates 78 and 83 are bores 94 which are dimensioned slightly larger than the diameter of the drive rod 27. A slot 96 communicates the end 98 of the drive plate 78 with the bore 94 such that bolts 99, which threadedly traverse the ends of the drive plate 78 and the slot 96, securely clamp the plate 78 to the drive rod 27. Similarly, the drive plate 83 is adapted to be securely clamped to an opposite end of the drive rod 27.

The drive rod 27 is journalled so as to be axially slideable in bushings 100 mounted in a pair of uprights or stanchions 101 which are rigidly secured to the plate 57 whereby the bellows 41 and 43 are maintained in axial alignment with the flow channel 47.

The reservoir 45 is adhesively secured to the top of the block 39. Immediately below the reservoir 45, a cavity 107 is formed in the block 39 such that a relatively narrow bridge 109 of material remains between the cavity 107 and the flow channel 47.

In an actual operation of the ultrasound calibrator apparatus 1, a fluid 105 containing suspended particles, constructed of polystyrene or other suitable material, is introduced through one of the fill ports 86 into the composite cavity 87. Simultaneously, the opposite port 86 is utilized as a vent to bleed air from the composite cavity 87. In the illustrated embodiment, the fluid 105 is distilled water, with suspended particles (such as polystyrene microspheres supplied by Polyscience, Inc., of Warrington, PA) having dimensions on the order of 6 microns, is used as the calibrating fluid. The filling process is continued until the composite cavity 87 is entirely filled with liquid 105 and all air is bled therefrom and then the ports 86 are sealed by the plugs 85. The reservoir 45 is also partially filled with a liquid 106 such as distilled water.

Thereafter, the motor 7 is started which actuates rotation of the cam 13. The speed of rotation of the cam 13 is monitored by the tachometer sensor 33 and equipment associated therewith. Rotation of the cam 13 is adjusted to a predetermined rate of rotation.

As the cam 13 rotates, the crank arm 8 operating through the reciprocating shaft 9 causes the drive rod 27 to oscillate back and forth longitudinally along the axis of the drive rod 27, as guided by the stanchions 101 indicated by the arrow in FIG. 4. When the cam shaft 17 is in the extreme right position, as shown in FIG. 3, the bellows 41 are substantially distended and the bellows 43 are substantially compressed. As the cam 13 continues to rotate, the cam shaft 17 periodically assumes the extreme left position, as shown in FIG. 4. In the latter configuration, the bellows 41 are substantially compressed while the bellows 43 are substantially distended. In the illustrated embodiment, the displacement between such extreme right position and such extreme left position is approximately one-half inch.

As the system 1 changes from the configuration shown in FIG. 3 to the configuration shown in FIG. 4, the bellows 41 and 43 function synchronously with one another through the rigid interconnection of the drive plates 78 and 83 with the rail 92 and the drive rod 27, such that fluid 105 contained in the bellows 41 is pressurized while the fluid 105 contained in the opposite bellows 43 is depressurized, thus forcing the fluid 105 between the bellows 41 through the channel 47 and into the bellows 43 in the direction indicated by arrow in FIG. 6. Conversely, as the system 1 oscillates back from the configuration shown in FIG. 4 to the configuration shown in FIG. 3, the fluid 105 is forced from the bellows 43 through the channel 47 to the bellows 41 as indicated by arrow in FIG. 7. The screens 51 serve as flow guides to produce a non-turbulent, laminar flow of the fluid 105 through the channel 47.

From the known values of the mean diameter of the bellows 41 and 43, and the radius of the flow channel 47 through the block 39, a mathematical relationship that is preestablished describes the velocity profile of the fluid 105 flowing through the channel 47 as a function of the rotational speed of the motor 7. Once the velocity characteristic of the channel 47 has been determined, the present invention, which operates on mechanical volume displacement techniques, avoids the functional dependencies such as type of fluid, fluid temperature, pressure and flow rate.

An ultrasound probe 116 of ultrasound equipment 117 containing transmit and receive capabilities is submerged in the fluid 106 contained in the reservoir 45, as illustrated in FIGS. 6 and 7, and the ultrasonic output therefrom is beamed into the flow channel 47. The probe 116 may be raised or lowered as required to appropriately space the probe 116 from the channel 47 to accommodate the various requirements of different types of ultrasound equipment. The ultrasonic frequency of the equipment 117 to be calibrated should be set sufficiently high to provide good power of resolution while avoiding excessively high frequencies in order to avoid corresponding excessively large transmission losses.

Such ultrasound equipment 117 can usually be operated in two modes. In its b-mode, the ultrasound equipment 117 can be used to determine the interior structure of the block 39 and to characterize the size of the flow chamber 47. (This usage of the present invention can be conducted prior to initiating the oscillatory flow between the bellows 41 and 43).

In its doppler mode, the ultrasound equipment 117 is used to measure the velocity profile of the flow of fluid 105 through the channel 47. The experimentally determined flow rate as measured by the ultrasound equipment 117 is then compared with the calculated velocity of the flow of fluid through the channel 47 as determined mathematically as aforesaid. (Preferably the peak or maximum velocities of the profiles are compared).

The calibration of such equipment 117 is then adjusted accordingly to eliminate any discrepancies between the measured and the calculated flow velocities.

Alternatively, commercially available pads saturated with liquid or gel may be used as an interface to regulate the intensity of the ultrasound signal radiated into the flow channel and thereby eliminate the need for the reservoir. This alternate approach would also avoid encroachment of fluid into the probe of the ultrasound equipment being calibrated.

It is to be understood that while certain forms of the present invention have been illustrated and described herein, it is not to be limited to the specific forms or arrangement of parts described and shown.

What is claimed and desired to be secured by Letters Patent is as follows:

1. A calibration apparatus for calibrating the doppler mode of operation of ultrasound equipment, the apparatus comprising:
   (a) a fluid flow channel having known cross-sectional area;
   (b) a pair of bellows flow communicating with each other through said channel; each of said bellows and channel containing a fluent medium; each of said bellows adapted to oscillatorily convey said fluent repetitively between both of said bellows through said channel;
   (c) motor means operably connected to both of said bellows;
   (d) mechanical linkage means operably translating movement of said motor means to both of said bellows so as to produce oscillatory flow of the fluent medium between both of said bellows at a selected velocity; and
   (e) a reservoir containing a liquid in close proximity to said channel; said reservoir adapted to receive a probe of the ultrasound equipment for determining the flow of said fluent medium in said channel so as to compare said selected velocity to that determined by the ultrasound equipment to allow calibration of the ultrasound equipment.

2. The calibration apparatus according to claim 1 including:
   (a) at least one screen portioned in said channel and adapted to produce laminar flow of the said fluent medium through said channel.

3. The calibration apparatus according to claim 2 including:
   (a) particulate matter suspended in said fluent medium.

4. The calibration apparatus according to claim 3 wherein:
   (a) said particulate matter has an average diameter of approximately 6 microns.

5. The calibration apparatus according to claim 3 wherein:
   (a) the distal ends of each of said pair of bellows are each adapted for rigid, fluid-tight securement to a first drive plate and a second drive plate, respectively.

6. The calibration apparatus according to claim 5 wherein:

(a) said distal ends of each of said bellows are each rigidly secured to an oscillatorily driven drive rod; and
   (b) a pair of uprights operatively constraining said drive rod to axial motion.

7. The calibration apparatus according to claim 6 including:
   (a) a rail rigidly secured to said first and second drive plate cooperating with said drive rod to operably maintain said first and second bellows in alignment with said channel.

8. The calibration apparatus according to claim 7 wherein:
   (a) said channel is constructed of polyvinylidenedifluoride.

9. The calibration apparatus according to claim 3 wherein:
   (a) said particulate matter is constructed of polystyrene.

10. A method for calibrating the doppler mode of ultrasound equipment comprising the steps of:
    (a) connecting first bellows means in flow communication through a channel having a known cross-sectional area with second bellows means;
    (b) repetitively transferring a fluent medium back and forth between said first and second bellows means through said channel such that the velocity profile of said fluent medium through said channel is known;
    (c) positioning a probe from the ultrasound equipment in close proximity to said channel;
    (d) beaming the output from said probe into said fluid being transferred; and
    (e) adjusting the magnitude of the velocity profile of the fluent medium as measured by the ultrasound equipment to coincide with the said known velocity profile of the fluent medium.

11. A calibration apparatus for calibrating ultrasound equipment, the apparatus comprising:
    (a) driving means for propelling a fluent medium at a selected velocity; said driving means comprising a motor and a pair of opposed bellows synchronously driven by said motor to propel the fluent medium through said conduit means;
    (b) conduit means adapted to convey the fluent medium at said selected velocity; and
    (c) interfacing means adapted to cooperate with the ultrasound equipment such that the ultrasound equipment measures said selected velocity of the fluid so as to allow calibration of the equipment.

12. The calibration apparatus according to claim 11 wherein:
    (a) said conduit means comprises a channel through a block constructed of material having a relatively low acoustical impedance, said channel positioned between and in flow communication with both of said pair of said bellows.

13. The calibration apparatus according to claim 12 wherein:
    (a) said interfacing means comprises a reservoir of fluid adapted to operably contain a probe of the ultrasound equipment to be calibrated mounted in relatively close proximity to said channel.

* * * * *